(12) United States Patent
Goetz et al.

(10) Patent No.: US 10,010,415 B2
(45) Date of Patent: Jul. 3, 2018

(54) APPARATUS COMPRISING INDIVIDUAL SHAFT FIBERS AND SET FOR FOLDING OR UNFOLDING A MEDICAL IMPLANT AND METHOD

(75) Inventors: Wolfgang Goetz, Regensburg (DE); Hou-Sen Lim, Singapore (SG)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 1382 days.

(21) Appl. No.: 13/996,542

(22) PCT Filed: Dec. 19, 2011

(86) PCT No.: PCT/EP2011/006410
§ 371 (c)(1),
(2), (4) Date: Sep. 5, 2013

(87) PCT Pub. No.: WO2012/084178
PCT Pub. Date: Jun. 28, 2012

(65) Prior Publication Data
US 2013/0338755 A1 Dec. 19, 2013

Related U.S. Application Data

(60) Provisional application No. 61/424,706, filed on Dec. 20, 2010.

(30) Foreign Application Priority Data

Dec. 20, 2010 (DE) .................. 10 2010 061 371

(51) Int. Cl.
A61F 2/06 (2013.01)
A61F 2/24 (2006.01)
A61F 2/95 (2013.01)

(52) U.S. Cl.
CPC .......... *A61F 2/2427* (2013.01); *A61F 2/2439* (2013.01); *A61F 2/95* (2013.01); *A61F 2002/9511* (2013.01)

(58) Field of Classification Search
CPC ............ A61F 2002/9511; A61F 2/2439; A61F 2/2427; A61F 2/95
USPC ........................................................ 623/1.11
See application file for complete search history.

(56) References Cited

U.S. PATENT DOCUMENTS

| 4,909,789 A | 3/1990 | Taguchi et al. |
| 5,824,055 A * | 10/1998 | Spiridigliozzi ......... A61F 2/954 |
| | | 606/195 |
| 2005/0075584 A1 | 4/2005 | Cali |
| 2005/0137695 A1 | 6/2005 | Salahieh et al. |
| 2005/0143809 A1 | 6/2005 | Salahieh et al. |

(Continued)

FOREIGN PATENT DOCUMENTS

| DE | 10 2006 057 216 A1 | 6/2007 |
| EP | 0 557 963 A1 | 9/1993 |

(Continued)

*Primary Examiner* — Christopher L Templeton
*Assistant Examiner* — Majid Jamialahmadi

(57) ABSTRACT

An apparatus for folding or unfolding at least one medical implant by way of at least one tension thread includes a shaft and a tensioning device for altering a form or shape of the foldable and/or unfoldable implant by way of the tension thread (11, 11'). In at least one shaft section thereof, the shaft includes a plurality of individual shaft fibers.

13 Claims, 5 Drawing Sheets

(56) References Cited

U.S. PATENT DOCUMENTS

| | | |
|---|---|---|
| 2006/0235509 A1* | 10/2006 | Lafontaine ............ A61F 2/2418 623/2.11 |
| 2007/0100427 A1 | 5/2007 | Perouse |
| 2007/0208214 A1 | 9/2007 | Hjelle et al. |
| 2007/0233223 A1 | 10/2007 | Styrc |
| 2009/0030512 A1* | 1/2009 | Thielen ................ A61F 2/2418 623/2.14 |
| 2010/0049313 A1 | 2/2010 | Alon et al. |
| 2010/0069930 A1 | 3/2010 | Roslin et al. |

FOREIGN PATENT DOCUMENTS

| | | |
|---|---|---|
| GB | 2 459 902 A | 11/2009 |
| JP | 2001-29478 A | 2/2001 |
| JP | 2008-536581 A | 9/2008 |
| JP | 2010-531709 A | 9/2010 |
| JP | 2010-534509 A | 11/2010 |
| WO | 2007/097983 A2 | 8/2007 |
| WO | 2009/002548 A1 | 12/2008 |
| WO | 2009-014617 A1 | 1/2009 |
| WO | 2009/094189 A1 | 7/2009 |
| WO | 2009/109348 A1 | 9/2009 |
| WO | 2010/022138 A2 | 2/2010 |

* cited by examiner

I-I

II-II

III-III

APPARATUS COMPRISING INDIVIDUAL SHAFT FIBERS AND SET FOR FOLDING OR UNFOLDING A MEDICAL IMPLANT AND METHOD

CROSS-REFERENCE TO RELATED APPLICATIONS

This application is filed under 35 U.S.C. 371 as a U.S. national phase application of PCT/EP2011/006410, having an international filing date of 19 Dec. 2011, which claims the benefit of U.S. Provisional Patent Application No. 61/424,706, having a filing date of 20 Dec. 2010, and German Patent Application No. 10 2010 061 371.1, having a filing date of 20 Dec. 2010, all of which are hereby incorporated by reference.

TECHNICAL FIELD

The present invention relates to an apparatus for folding or unfolding an implant and a set. It further relates to a method.

BACKGROUND

From practice, implants are known that can be folded and/or unfolded by means of one or more threads transferring tension onto the implant. Furthermore, respective apparatuses for folding and unfolding are known from practice.

One object of the present invention is to propose a further apparatus for folding or unfolding a foldable and/or unfoldable implant by means of a tension thread. Furthermore, an appropriate set comprising such an apparatus, as well as a method for folding and/or unfolding an implant are to be proposed.

SUMMARY

Thus, according to the present invention, an apparatus for inserting and/or folding and/or unfolding an implant by means of at least one tension thread is proposed. The apparatus according to the present invention comprises a shaft.

Furthermore, the apparatus comprises at least one tensioning device for altering a form or shape, a geometry or a folding state of the foldable and/or unfoldable implant by means of the at least one tension thread.

The shaft of the apparatus comprises in at least one shaft section thereof a plurality of individual shaft fibers.

Embodiments according to the present invention may each comprise one or more of the following features in any arbitrary combination.

In some embodiments of the apparatus according to the present invention, altering a form or shape of the implant means reducing or increasing a diameter, in particular an outer diameter, of the implant. Alterations of the diameter may be accompanied by any kind of alteration of the implant's length or any other alteration, or may be not.

In certain embodiments of the apparatus according to the present invention, folding the implant means reducing the implant's diameter.

In some embodiments according to the present invention, folding is to be understood as increasing a diameter of the implant.

In certain embodiments according to the present invention, the implant's diameter is present in a plane perpendicular to a main flow direction of the implant, in case the implant is flown through by a fluid after its implantation.

In some embodiments of the apparatus according to the present invention, the at least one tension thread is a thread or filament or yarn, respectively. It can be designed or embodied similar to a surgical sutural thread or it can be such a surgical sutural thread. It can be designed or embodied as a rope or a cord or twine or string, respectively. It can be designed or embodied as a chain comprising a plurality of chain members engaged with adjacent chain members.

In the following, whenever reference is made to a thread or tension thread, the terms may include a plurality of threads or tension threads as well insofar as a person skilled in the art recognizes the exchangeability of the terms.

In certain embodiments, the shaft of the apparatus is in at least one section thereof embodied rigidly. In some embodiments, the shaft of the apparatus is in at least one section thereof embodied such as to be bendable in one or more directions (i.e. it may be bent in a longitudinal direction or in a direction of the shaft's width, in both directions or in any other direction). In some embodiments, the shaft is embodied extendably or stretchably. In other embodiments, the shaft is embodied stiffly or inflexibly.

In one embodiment of the apparatus according to the present invention, during its implanted implantation state, the implant is able to be penetrated by fluids or is permeable for fluids, respectively, in its longitudinal direction. The terms "permeable" or "able to be penetrated" hereby refer to the ability of the implant to be penetrated or flown through by fluids.

In some embodiments of the apparatus according to the present invention, in the moment of unfolding or folding, the implant is loosely arranged or attached to or at or on a receiving area of the apparatus. In some embodiments according to the present invention, the implant is thereby connected with the receiving area only by means of the tension threads.

In certain embodiments of the apparatus according to the present invention, the tension thread comprises or consists of a bundle or a plurality of threads or thread elements.

In some embodiments according to the present invention, a shaft fiber of the apparatus is permeable or patent (like a blood vessel) within its interior in at least sections of its longitudinal direction or along its entire length. In those embodiments, the shaft fiber comprises a wall.

In certain embodiments, at least one of the tension threads (or all of them) is partly arranged within an inner space of the respective shaft fiber and extends from there to an outside of the shaft fiber through the shaft opening.

In some embodiments, at least one of the tension threads (or all of them) exits from an inner space of the shaft fiber through one shaft opening. In other embodiments, at least one of the tension threads (or all of them) exits from the inner space through two or more shaft openings.

In certain embodiments according to the present invention, the at least one shaft opening is provided at or on the front surface of the shaft fiber. In other embodiments according to the present invention, it is arranged at or on a circumferential surface or lateral surface area of the shaft. Preferably, the shaft opening is arranged in or within a tip area of the shaft fiber or in or within a proximal area of the shaft fiber.

In certain embodiments according to the present invention, the shaft fiber comprises a plurality of shaft openings uniformly or non-uniformly distributed or arranged along or about a periphery or along or about a circumferential surface or lateral surface area of the shaft or of the shaft fiber.

Additionally or alternatively, the shaft openings may be dispersed along or about a longitudinal direction of the shaft or of the shaft fiber. For example, in some embodiments according to the present invention, shaft fibers may have two or more shaft openings which are arranged under different distances between the respective opening and the tip or one end of the corresponding shaft fiber.

In certain embodiments according to the present invention, at least one or all of the shaft fibers are arranged such that they do no move relatively to the apparatus according to the present invention in a longitudinal direction of the apparatus upon folding or unfolding the medical implant.

In some embodiments according to the present invention, tension threads for folding and/or unfolding the implant enter and/or exit through the shaft opening.

In certain embodiments according to the present invention of the apparatus, during the use of the apparatus, shaft fibers of the plurality of individual shaft fibers are always present in bundled form in at least one first section of the shaft section. In contrast, in a second section, they are provided for moving or drifting away from each other during use of the apparatus.

In some embodiments according to the present invention, the second section is closer to the tip of the apparatus than the first section.

In certain embodiments according to the present invention, the first section directly merges with or passes over into the second section.

In some embodiments according to the present invention, the individual shaft fibers are arranged in contact to each other in the first section such that there is no lumen such as, e.g., a central lumen, for example a lumen usable during the use of the apparatus for fulfilling particular functions, provided between the shaft fibers in the first section. Spoken differently, the shaft fibers are arranged closely or at close quarters.

In some embodiments according to the present invention, the term "individual shaft fibers"—when used discretely—comprises all shaft fibers present of the plurality of the entirely present individual shaft fibers; in other embodiments, it only comprises some of them.

In certain embodiments according to the present invention, the number of individual shaft fibers is set to two shaft fibers; in other embodiments, the number is set to three, four, five, six, seven etc. The number may be a great number; it may exceed ten or twenty and comprises every natural number up to at least 30 or 40.

A great number of individual shaft fibers advantageously allows for separating the part or rim portion of the implant (for example, the periphery of the implant) which experiences an action by means of the tension threads for folding/unfolding, that exit from the individual shaft fibers into a great number of subunits. The inventors of the present invention have recognized that, for example, dividing the periphery into many but small or short sectors or rim portions upon attaching the tension threads at or on the implant, in certain embodiments, favors a uniform folding or unfolding the implant. Additionally, such dividing into a great number of sections may advantageously avoid any buckling or bulging or denting of the periphery.

A great number can be any numerical value between 3 and 40, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40. Greater values are encompassed by the present invention as well.

In some embodiments according to the present invention, neither the individual shaft fibers nor sections thereof are arranged within the interior or material of a wall of an envelope, an outer boundary or limitation, or the like of the apparatus.

In certain embodiments according to the present invention of the apparatus, the individual shaft fibers are provided such that they cannot be shifted or moved relative to the remainder of the apparatus in a longitudinal direction thereof.

In some embodiments according to the present invention of the apparatus, shaft fibers of the plurality of individual shaft fibers each comprise one or more shaft openings. The one or more tension threads can enter into and/or exit from the respective shaft fiber through the shaft openings.

In certain embodiments according to the present invention, such shaft openings are solely provided for allowing tension threads to enter in or into and/or leave or exit from the respective individual shaft fiber.

In some embodiments according to the present invention, the individual shaft fibers are designed or embodied to comprise one or more through-openings (extending into a longitudinal direction of the shaft fiber) or one or more hollow interiors. These through-openings or hollow interiors may allow guiding one or more tension threads through the shaft fiber, e.g. from the tensioning device of the apparatus to a shaft opening or to an exit opening at the tip portion of the shaft fiber.

In some embodiments according to the present invention, the tension threads are arranged within an interior of the shaft fibers such that they can be shifted or moved relative to the respective shaft fibers.

In some embodiments according to the present invention, the individual shaft fibers and/or the tension threads do not comprise any devices for establishing a hook engagement with the implant.

In some embodiments according to the present invention, some or all of the tension threads are connected with the implant by solely entangling or entwining the implant or a part or section or portion thereof.

In certain embodiments according to the present invention of the apparatus, during a state of use of the apparatus, shaft fibers of the plurality of individual shaft fibers are arranged movably in or forth from (in the direction towards the tip of the apparatus) at least the second section of the shaft respectively independently of each other and/or independently of the position of the implant relative to the apparatus for folding or unfolding. Differently spoken, they can move away from each other and/or move towards each other in or within the second section.

In some embodiments according to the present invention of the apparatus, the shaft comprises in at least one section thereof a device for bundling individual shaft fibers of the plurality of individual shaft fibers.

In certain embodiments according to the present invention, there are provided more than just one device for bundling (but two, three, four, and so on, devices of this kind). Additionally or alternatively, in some embodiments, the device for bundling comprises not just one means, e.g. having the shape of a collar, but more than one means (e.g., two, three, four, and so on, means).

In certain of the embodiments comprising more than one device for bundling or means for bundling, the individual devices or means are provided on the shaft fibers while being spaced apart from each other. The particular space or distance chosen or set may advantageously contribute to setting or predetermining the stiffness, bendability and other mechanical features of the shaft fibers. This may be true for the shaft fibers' parts arranged between the devices or means for bundling. It may also be true for the parts of the shaft fibers that are not bundled but allowed to move freely with regard to each other.

In some of the embodiments comprising more than one device for bundling or means for bundling, a (that is, one or more) core element or a (that is, one or more) interconnecting element is provided on, at or within the bundle of shaft fibers. The core element or interconnecting element may also advantageously contribute to setting or predetermining the stiffness, bendability and other mechanical features of the shaft fibers. The core element or interconnecting element may be attached to one, two or all of the devices or means for bundling. However, it may not be attached as well. The core element or interconnecting element may be provided to be extendable and to change its length, for example, when a distance between neighbouring, adjacent or interacting devices for bundling or means for bundling is changed or adapted to need.

Both providing more than only one device for bundling or means for bundling and providing a core element or the like may in certain embodiments of the present invention allow for keeping the shaft fibers in parallel in use along a certain or even predetermined distance. Again, this may also advantageously contribute to setting or predetermining the stiffness, bendability and other mechanical features of the shaft fibers, both in the vicinity of core element or device or means for bundling and also in the second section of the shaft in which the shaft fibers are intended to move, wander or migrate freely in case of need.

In certain embodiments according to the present invention, the device for bundling is designed or embodied as a ring encompassing the individual shaft fibers to be bundled and inhibiting the shaft fibers from drifting or moving away from each other. In some embodiments according to the present invention, the device for bundling is designed or embodied as a clamp, a protrusion or a constriction of the apparatus, or the like.

In certain embodiments according to the present invention of the apparatus, the device for bundling individual shaft fibers is arranged to be shiftable along a longitudinal extension of the apparatus. Additionally or alternatively, the device for bundling may be alterable or manipulatable or engineerable in any other way. For example, the device for bundling may be manipulated by setting or altering a gap or play between shaft fibers and the device for bundling limiting or encircling the shaft fibers. Additionally or alternatively, the device for bundling can be provided for being used at or on different sections of the apparatus along the longitudinal extension thereof. The afore-mentioned manipulations may advantageously alter or adapt to the need, respectively, the stiffness or rigidity of the individual shaft fibers in or within the second section.

In other embodiments, a device for bundling such as specified above is not provided. In some embodiments, it is not possible to distinguish a first section from a second section (such as specified above and below) or required.

In some embodiments according to the present invention of the apparatus, individual shaft fibers are designed or embodied and provided or prepared for moving or bending or tilting, or the like, towards a rim portion of the implant when applying tension onto the implant by means of the tension thread extending through the said individual shaft fiber.

"Moving towards" is in some embodiments to be understood as a deviation of at least one section of the individual shaft fiber (mainly in the second section or in a tip area of the individual shaft fiber) from a position that is arranged closer to a center of a cross section of the apparatus according to the present invention into a position that is arranged more radially as compared to the first position, e.g. into a rim area or towards a rim portion.

In certain embodiments according to the present invention the bundle of shaft fibers can be (or are) arranged in a circular manner.

In some embodiments according to the present invention, the shaft fibers (e.g. nine shaft fibers in total) are arranged in a circular manner in both the unfolded and/or the folded state of the medical implant.

In certain embodiments according to the present invention, a rim portion is a section that is present in an area of an—in relation to the implant—exterior wall or envelope.

In some embodiments according to the present invention, the rim portion comprises a part of the foldable material of the implant. The rim portion may be a curve-shaped part of an outer limitation or of a wall (e.g. a mesh, grid, strut or bar structure) of the implant. The rim portion may be a tart-like structure.

In certain embodiments according to the present invention of the apparatus, tension threads exiting from individual shaft fibers are connected with a rim portion of the implant for applying a force onto the implant.

In some embodiments according to the present invention, the rim portion which is folded or unfolded by means of a particular shaft fiber or by means of the one or more tension threads of the shaft fiber, respectively, is only a part of the foldable and/or unfoldable periphery of the implant. In those embodiments, the rim portion does not comprise the entire periphery, whereas, in other embodiments, it indeed does.

In certain embodiments according to the present invention of the apparatus, tension threads exiting from individual shaft fibers are connected with a rim portion of the implant for applying a force onto the rim portion. In certain embodiments according to the present invention, tension threads exiting from at least two or more individual shaft fibers are connected with the said rim portion, or parts thereof.

In some embodiments according to the present invention of the apparatus, tension threads exiting from individual shaft fibers are connected with a rim portion in an overlapping manner for applying a force onto the rim portion of the implant. In those embodiments, it is intended to fold or unfold a particular rim portion or a part thereof by means of two, three or more tension threads exiting from different individual shaft fibers. In this way, an overlap of several tension threads is achieved in an area of a particular rim portion. This may advantageously contribute to a more uniform folding of the implant.

In certain embodiments according to the present invention of the apparatus, tension threads exiting from individual shaft fibers are connected with differently large, broad, long or in any other way different rim portions of the implant for applying a force on the said rim portions. Thus, a first rim portion may have a first arc or curve length x, a second rim portion may have a second arc or curve length 2x. This may advantageously allow for or contribute to a more uniform folding of the implant even in cases in which the implant does not behave in a mechanically uniform way over its entire periphery upon folding.

In some embodiments according to the present invention, the apparatus is designed or intended for folding and/or unfolding an implant designed as a stent or a heart valve arrangement.

The object according to the present invention is also solved by means of the set according to the present invention. The set according to the present invention comprises at least one apparatus according to the present invention and at least one implant that is connected with tension threads for the purpose of being folded and/or unfolded or that is provided or prepared for being connected therewith.

In some embodiments of the set according to the present invention, the implant is a stent or a heart valve arrangement.

In certain embodiments of the set according to the present invention, individual shaft fibers on the one hand and the implant on the other hand are adapted, chosen or fit to each other as regards their mechanical properties. In certain embodiments according to the present invention, this may be effected such that, during the process of folding the implant, a first force or tension required for moving the shaft fibers in a section thereof, in particular in an area of a shaft opening for tension threads, from their longitudinal alignment or in a direction of the radial extension of the implant is lower than a second force or tension. The second force or tension is a force or tension required for effecting a folding or the beginning or an appreciable beginning of a folding of the implant by means of the tension threads connected with the implant that exit from the shaft openings. Said in a more simple manner, in some of those embodiments, upon application of tension, the individual shaft fiber firstly moves in a—for example, radial—direction towards a rim portion of the implant upon applying tension by means of the tension threads exiting from the shaft fiber, prior to beginning any folding of the respective rim portion. This adaptation or adjustment of properties of the individual shaft fibers (such as bendability, flexibility, elasticity, or rigidity) with respect to the properties of the implant may ensure that, upon applying tension by means of the tensioning device, the individual shaft fibers firstly automatically move into a position in which the force applied or to be applied by means of the tension thread is applied onto the implant or onto the rim portion in or under a desired angle.

In some embodiments according to the set according to the present invention of, the implant is connected or intended to be interconnected with the apparatus by means of tension threads such that the tension threads (independently of each other or in an overlapping manner) interconnect with a great number of peripheral sections of the implant. A great number may be any numerical value between 3 and 40, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40. Greater values are encompassed by the present invention as well.

In some embodiments of the set according to the present invention, the implant is connected or intended to be interconnected with the apparatus by means of tension threads such that the tension threads may act and/or contact the medical implant not only at one end of the medical implant but at least at two or more sections of the medical implant which are longitudinally offset from each other.

The object according to the present invention is further solved by means of the method according to the present invention. The method according to the present invention is or comprises the use of an apparatus according to the present invention or of a set according to the present invention.

In certain embodiments of the method according to the present invention, the method comprises altering a tension applied onto the implant by means of at least one tension thread. The tension is controlled by means of altering a length of the one or more tension threads exiting from the interior of the shaft or of the shaft fiber.

In some embodiments of the method according to the present invention, the method comprises shifting or otherwise manipulating or engineering the device for bundling individual shaft fibers. In this way, the rigidity, stiffness, elasticity, or the like, of the respective individual shaft fibers may be set according to need—in particular with regard to the second section.

In some embodiments of the method according to the present invention, prior to its implantation, the implant is connected with the apparatus by means of tension threads such that the tension threads (independently of each other or in an overlapping manner) interconnect with a great number of peripheral sections of the implant. A great number may be any numerical value between 3 and 40, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40. Greater values are encompassed by the present invention as well.

The advantages achievable by means of some or all embodiments of the apparatus according to the present invention may also be obtained by means of the set according to the present invention and the method according to the present invention.

Some or all of the following advantages and the advantages mentioned above can be achieved in some, certain or all embodiments according to the present invention.

In some embodiments according to the present invention, one advantage achievable according to the present invention is to advantageously reduce or even completely avoid buckling or bulging or denting of the implant resulting from applying a force onto the implant—mainly onto the periphery thereof—by means of the tension threads.

Another advantage is a uniform folding of the implant even in a case in which an implant is designed inhomogeneously as regards the mechanical properties of the implant along the periphery thereof.

According to yet another advantage—due to the capacity of the individual shaft fibers to move, migrate or wander—the tension threads' exit from exit openings of the shaft fibers may be effected in or under angles at which the tension threads will not suffer particular friction or shear stress at the exit or shaft openings. In connection therewith, a further advantage could be that the force for folding—again due to the possibility of the individual shaft fibers to move, migrate or wander—is acting on the implant under particularly advantageous angles.

BRIEF DESCRIPTION OF THE DRAWINGS

In the following, the present invention will be exemplarily described with respect to the appended drawing. In the drawing, same reference numerals refer to same or identical elements. In the drawings:

FIG. 1b shows a section along the line I-I of FIG. 1a;

FIG. 2b shows a section along the line II-II of FIG. 2a;

FIG. 3b shows a section along the line III-III of FIG. 3a;

DETAILED DESCRIPTION

Figure 1A:
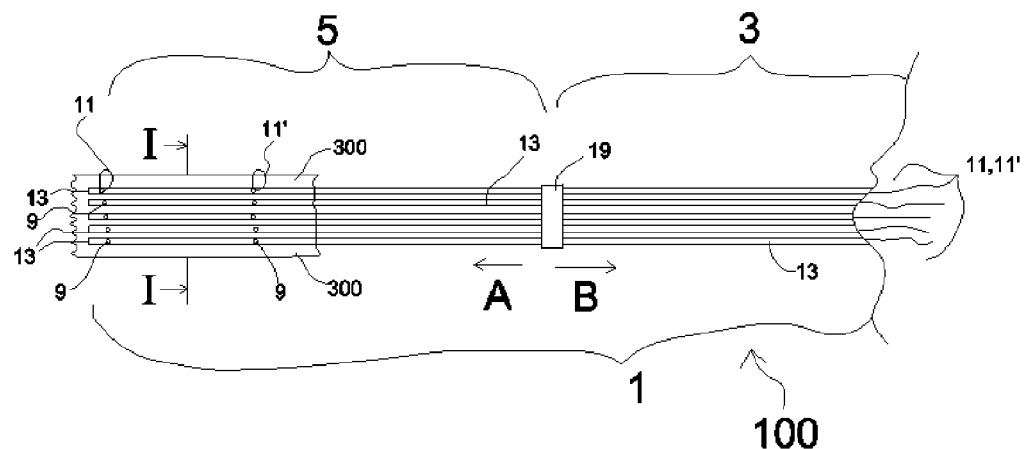
FIG. 1a shows a partial longitudinal section through an apparatus according to the present invention, a section of which is shown in a schematically simplified manner, prior to unfolding the implant.

FIG. 1 shows a partial longitudinal section through an apparatus 100 according to the present invention that is shown in a schematically simplified manner and only in a section thereof. The apparatus 100 comprises a shaft 1 comprising a first section 3 and a second section 5. A plurality of individual shaft fibers 13 extends along or about both the first section 3 and the second section 5. The first and the second section 3, 5 may be referred to as shaft section.

The individual shaft fibers 13 comprise shaft openings 9. Merely exemplarily, FIG. 1a shows two tension threads 11 and 11' each which exit from a shaft opening 9, twining or looping around a rim portion of the implant 300 shown in a folded state in FIG. 1a and—to be understood merely exemplarily as well—which re-enter into the same or into another shaft opening 9 of the same shaft fiber 13.

One tension thread or more tension threads 11 and 11' may exit from an interior of the shaft 1 towards the exterior of the shaft 1 through the shaft openings 9 and/or may enter in the opposite direction. In FIG. 1a, all threads 11 and 11' both exit and enter in a loop manner through the shaft openings 9.

The tension threads 11 and 11' are provided or intended to encompass an implant not shown in FIG. 1a such that the implant will have an altered diameter when altering the tension applied onto the threads 11 and 11' in sections thereof.

In the state of the implant 300 shown in FIG. 1a, the tension threads 11 and 11' are arranged at the implant 300 under tension by means of which they inhibit an undesired opening, unfolding or expansion of the implant 300 (the latter resulting, e.g., from a memory shape property of the implant).

FIG. 1a shows only two tension threads 11 and 11'. This serves for the purpose of clarity. However, a person skilled in the art will recognize that every shaft fiber 13 can comprise one or more of such tension threads. The latter can exit from the shaft fibers 13 at different heights thereof, wherein this applies both for one the same shaft fiber 13 and, e.g., adjacent shaft fibers 13.

As can be seen from FIG. 1a, the individual shaft fibers 13 arranged on the right side (i.e. away from the tip of the apparatus 100 or within the second section 5, respectively) of a device 19 for bundling individual shaft fibers 13 are combined or concentrated in a bundle. In the second section 5 (i.e. on the left side of the device 19 or towards the tip of the apparatus 100, respectively), the shaft fibers 13 are arranged freely movably—relative to each other, although, in the state of the implant 300 shown in FIG. 1a, they also contact each other—as they do also in section 5.

On the one hand, the device 19 for bundling allows for the bundled shaft fibers 13 in FIG. 1a to move freely in radial direction on the left side of the device 19. Thereby, they can follow the motion or movement or geometry of the unfolded implant 300. The device 19 is arranged not to hamper that movement.

On the other hand, the device 19 for bundling allows for setting the rigidity or stiffness of the shaft fiber 13 on the left side of the device 19. By shifting the device 19 along the shaft 1 to the left as indicated by arrow A in FIG. 1a, the rigidity or stiffness of the individual shaft fibers 13 beyond the device 19 can be increased. By shifting the device 19 in the direction indicated by arrow B (i.e., to the right side in FIG. 1a), the rigidity or stiffness of the shaft fiber 13 on the left side of the device 19 can be reduced. In this way, the apparatus 100 may advantageously be adapted to different features or behaviour of different implants.

It is obvious that the implant is represented in a very schematic and simplified manner. The present invention may be carried out with any implant designed or embodied to be foldable and/or unfoldable by means of tension threads upon implantation.

Figure 1B:
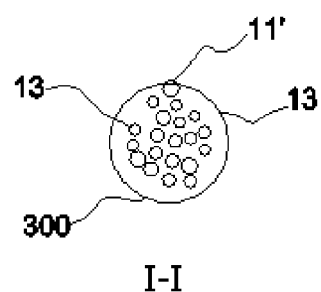

FIG. 1b shows a section along line I-I of FIG. 1a.

Figure 2A:
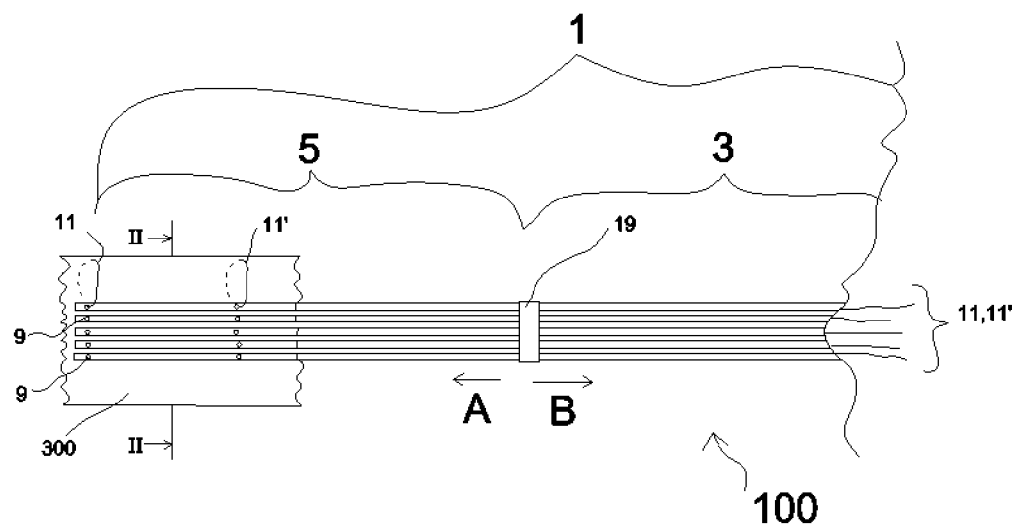
FIG. 2a shows a partial longitudinal section through the apparatus according to the present invention of FIG. 1a, a section of which is shown in a schematically simplified manner, after unfolding the implant, with tension-free tension threads.

FIG. 2a shows a partial longitudinal section through the apparatus 100 according to the present invention of FIG. 1a that is shown in a schematically simplified manner and only in a section thereof after having entirely unfolded the implant 300 with the tension threads 11 and 11' being completely or substantially released or free from tension.

The individual shaft fibers 13 are present in a bundled form on both sides of the device 19 (i.e., on the left side and on the right side of the device 19, i.e., both in the first section 3 and in the second section 5). In any case they are provided in a bundle in which the individual shaft fibers 13 are close to each other or even contact each other. Due to their form which they take on while not experiencing any external tension or force, the shaft fibers 13 are present in an extended or stretched form in the second section 5. This is possible because the tension threads 11 and 11' are getting longer or stretch upon (or after) opening or unfolding of the implant 300. The latter can be achieved by correspondingly actuating the tensioning device not shown in the figures.

Figure 2B:
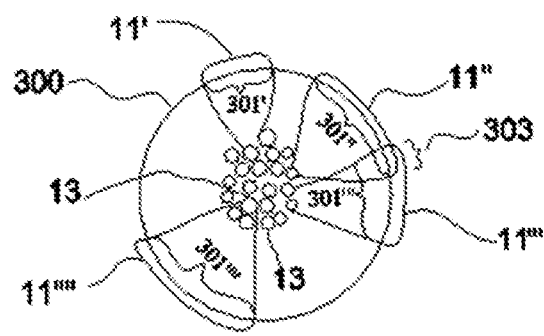

FIG. 2b shows a section along the line II-II of FIG. 2a. As can be recognized, the individual shaft fibers 13 are present in a bundle such as shown in FIG. 1b; however, they are only bundled loosely and are not pressed against each other by an external force.

Tension threads 11', 11", 11' and 11" that are shown by way of example each encompass a rim portion 301', 301", 301'" or 301"". In an area 303 of overlap both the tension thread 11" and the tension thread 11' are provided. According to the present invention, such an overlap can be provided at any position, in particular along the periphery, of the implant 300. Moreover, it can be designed in any arbitrary way: based on two tension threads, three tension threads etc. In some embodiments, a more uniform application of tension force for folding the implant may be achieved by means of such an overlap.

As is illustrated in FIG. 2b, the rim portions encompassed by tension threads may have different widths or lengths, yielding the advantages mentioned above.

Figure 3A:
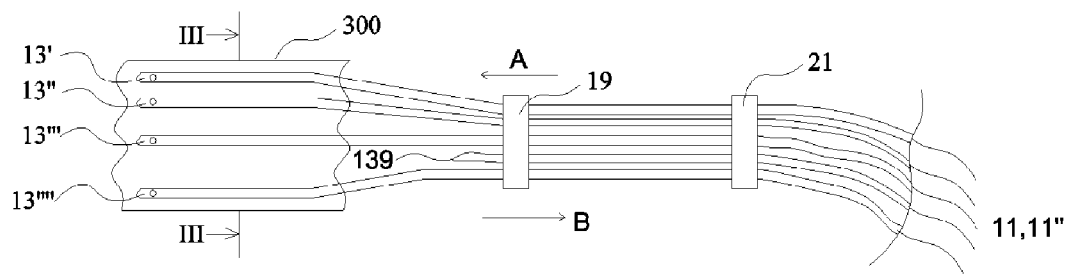
FIG. 3a shows a partial longitudinal section through the apparatus according to the present invention of FIG. 1a, a section of which is shown in a schematically simplified manner, after unfolding the implant with tensioned tension threads.

FIG. 3a shows a partial longitudinal section through the apparatus 100 according to the present invention of FIG. 1a that is shown in a schematically simplified manner and only in a section thereof after unfolding the implant 300 using tensioned tension threads. For example, four shaft fibers 13', 13", 13'" and 13"" are present within the implant 300. As can be seen from FIG. 3b in which an additional cut shaft fiber 139 is shown, the number of four shaft fibers is merely chosen for improved clarity and more than four shaft fibers may be present. However, a person skilled in the art will recognize the latter when considering the above specification.

Figure 3B:
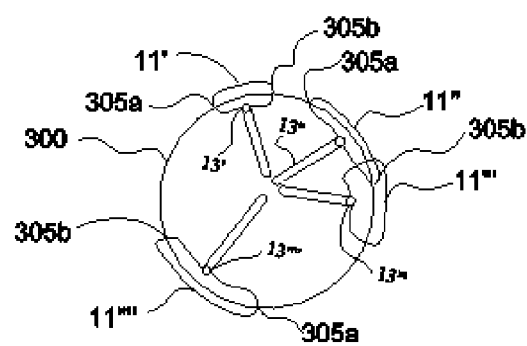

FIG. 3b shows a section along the line III-III of FIG. 3a.

It can readily be seen that, due to the tension applied by means of the respective tension threads 11', 11", 11'" and 11"", the shaft fibers 13', 13", 13''' and 13'''' have moved from the center of the implant 300 towards a rim area of the implant 300 or at least in a radial direction. One effect of this motion or movement is explained in detail with respect to FIGS. 4 and 5 below. However, without any further explanation, a person skilled in the art will yet be aware from FIG. 3b that the respective tension threads exit from the shaft fibers 13', 13", 13''' and 13'''' via the shaft openings in a substantially diametrical manner. Further, it can be recognized that the respective tension threads each extend between two penetration openings 305a and 305b that are present within the implant's periphery and at which the tension threads penetrate from the interior to the exterior through the "envelope" of the implant, on a more or less straight curve—together with the cross section of the shaft fiber.

In FIG. 3a, only by way of example, a second device for bundling depicted as reference numeral 21 is shown. As can be seen from FIG. 3a, the shaft fibers' portions situated between the two devices 19 and 21 are kept in parallel by means of the devices 19 and 21. On the right side of device 21 for bundling, the shaft fibers can flex or bend again.

Figure 4A:
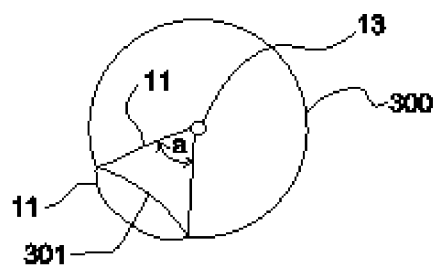
FIG. 4a, 4b in synopsis show an advantage achievable by means of some embodiments according to the present invention.
Figure 4B:
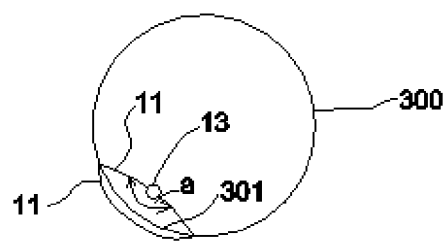

In synopsis with FIG. 4b, FIG. 4a shows one advantage achievable by means of some embodiments according to the present invention using a sectional view similar to that of FIGS. 1b, 2b and 3b.

FIG. 4a shows how a rim portion 301 may bulge or dent inwardly when the tension thread 11 entangled around it is guided by means of a shaft fiber 13 arranged in the center of the implant—as is often the case with conventional arrangements in certain constellations or apparatus-implant-arrangements. The inventors of the present invention have realized that such a bulging or denting—both inwardly and outwardly—including any undesired non-uniform folding of the implant as well largely depends on the angle α shown in FIG. 4a.

In contrast, FIG. 4b shows the alteration of angle α when the shaft fiber 13 is allowed to move, wander or migrate to or towards an outer area or the rim portion 301 of the implant 300 upon biasing or tensioning the tension thread 11. Bulging or denting inwardly or outwardly or non-uniformly folding the implant may hereby in certain settings under otherwise unchanged conditions advantageously be reduced or even excluded.

Figure 5A:
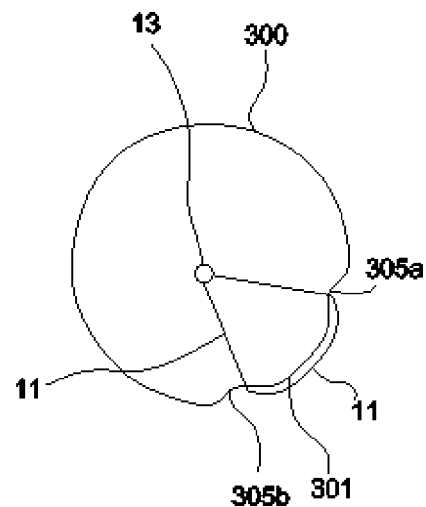
FIG. 5a, 5b in synopsis show a further advantage achievable by means of certain embodiments according to the present invention.
Figure 5B:
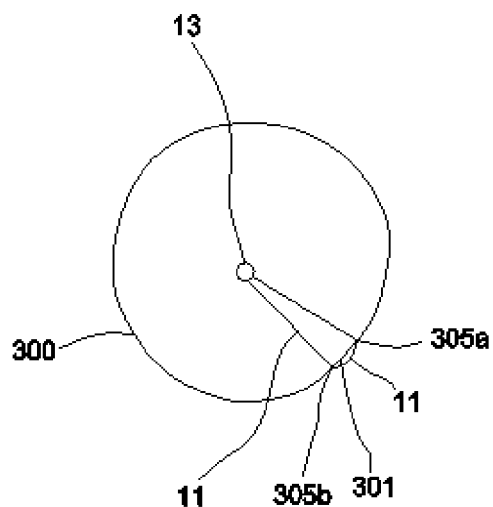

In synopsis with FIG. 5b, FIG. 5a shows a further advantage achievable by means of certain embodiments according to the present invention using a sectional view similar to that of FIGS. 1b, 2b, 3b and 4b.

FIG. 5a shows the effect a tension thread 11 may have onto the periphery or the rim portion 301 of an implant 300 when applying tension onto the periphery or the rim portion 301 by means of the tension thread 11.

In FIG. 5a, as in FIG. 3b, penetration areas 305a and 305b are shown. The tension thread 11 penetrates through the penetration areas 305a and 305b from a center of the implant to the exterior thereof, or vice versa. As can be seen in FIG. 5a, the penetration areas 305a and 305b may, due to the tension, bend or dent towards the center of the implant 300 or may fold non-uniformly with respect to the remaining periphery of the implant 300. As shown in FIG. 5a, this effect can be seen when the shaft fiber 13 is arranged in the center of the implant 300, an arrangement that is common in the state of the art. In certain embodiments, the same effect can also be seen when the shaft fiber 13 is arranged more radially.

A solution to the problem shown in FIG. 5a is shown in FIG. 5b. If the rim portion encompassed by the tension thread is set or determined to be sufficiently narrow or short (i.e. if the penetration openings 305a and 305b are arranged sufficiently close) such as proposed with respect to some embodiments according to the present invention, denting or bulging or a non-uniformly folding of the implant 300 can advantageously be avoided.

What is claimed is:

1. A set, comprising:
   a foldable and/or unfoldable medical implant, the medical implant being a stent or a heart valve arrangement; and
   an apparatus for folding or unfolding the medical implant by means of at least one tension thread, the apparatus comprising:
   a shaft adapted for attaching the medical implant;
   a tensioning device for altering a form or shape of the medical implant by means of one or more tension threads, the medical implant being connected with the one or more tension threads,
   wherein the shaft comprises in at least one shaft section thereof a plurality of individual shaft fibers,
   wherein the plurality of individual shaft fibers are configured to be unmovable relative to the remainder of the apparatus in a longitudinal direction thereof when the one or more tension threads are released or restricted,
   wherein individual shaft fibers of the plurality of shaft fibers and the medical implant are adapted such that, during a process of folding the medical implant, a first force required for moving the shaft fibers in a section thereof comprising shaft openings for the one or more tension threads, from their longitudinal alignment or for moving them in a direction of radial extension of the medical implant, is lower than a second force required for effecting folding of the medical implant by means of the one or more tension threads connected with the medical implant and which exit from the shaft openings.

2. The set according to claim 1, wherein, during use of the apparatus, shaft fibers of the plurality of individual shaft fibers are always present in bundled form in at least one first section of the shaft section, whereas, in a second section, the shaft fibers are provided or intended for moving away from each other during use of the apparatus.

3. The set according to claim 2, wherein the shaft fibers of the plurality of individual shaft fibers each comprise one or more shaft openings by means of which the one or more tension threads can exit from and/or enter into the respective shaft fiber.

4. The set according to claim 1, wherein shaft fibers of the plurality of individual shaft fibers each comprise one or more shaft openings by means of which the one or more tension threads can exit from and/or enter into the respective shaft fiber.

5. The set according to claim 4, wherein the shaft opening is arranged at or on a circumferential surface or lateral surface area of the shaft.

6. The set according to claim 4, wherein at least one shaft fiber of the plurality of shaft fibers comprises a plurality of shaft openings.

7. The set according to claim 1, wherein, during a state of use of the apparatus, shaft fibers of the plurality of individual shaft fibers are arranged movably in or forth from at least a section of the shaft independently of each other and/or independently of the position of the medical implant relative to the apparatus for folding or unfolding.

8. The set according to claim 1, wherein the shaft comprises in at least a section thereof at least one device for bundling individual shaft fibers of the plurality of individual shaft fibers.

9. The set according to claim 8, wherein the at least one device for bundling the individual shaft fibers is arranged to be shiftable or movable along a longitudinal extension of the apparatus or is otherwise alterable or manipulatable or engineerable and/or is provided or intended for being used at or on different sections of the apparatus along the longitudinal extension thereof.

10. The set according to claim 1 is configured as a heart catheter.

11. The set according to claim 1, wherein individual shaft fibers of the plurality of shaft fibers are configured to move towards a rim portion of the medical implant when applying tension onto the medical implant by means of the one or more tension threads extending through the individual shaft fibers.

12. The set according to claim 1, wherein two or more tension threads of the one or more tension threads exit from individual shaft fibers of the plurality of shaft fibers and are connected with a rim portion of the implant for applying a force onto the rim portion, wherein the rim portion only comprises a part of the foldable and/or unfoldable periphery of the medical implant.

13. The set according to claim 1, wherein the one or more tension threads exit from individual shaft fibers of the plurality of shaft fibers and are connected with a rim portion of the medical implant for applying a force onto the rim portion of the medical implant, wherein two or more of the one or more tension threads exit from at least two individual shaft fibers are connected with the rim portion or parts thereof.

* * * * *